United States Patent
Zhang et al.

(10) Patent No.: US 12,162,904 B2
(45) Date of Patent: Dec. 10, 2024

(54) MANNOSE DERIVATIVE AND APPLICATION THEREOF

(71) Applicant: Beijing Normal University, Beijing (CN)

(72) Inventors: Junbo Zhang, Beijing (CN); Qing Ruan, Beijing (CN); Guangxing Yin, Beijing (CN); Xuebin Wang, Beijing (CN); Zhanbin Zhang, Beijing (CN); Zhigang Tang, Beijing (CN); Jie Lu, Beijing (CN)

(73) Assignee: Beijing Normal University, Beijing (CN)

( * ) Notice: Subject to any disclaimer, the term of this patent is extended or adjusted under 35 U.S.C. 154(b) by 0 days.

(21) Appl. No.: 18/513,283

(22) Filed: Nov. 17, 2023

(65) Prior Publication Data

US 2024/0109929 A1    Apr. 4, 2024

Related U.S. Application Data

(63) Continuation of application No. PCT/CN2022/104832, filed on Jul. 11, 2022.

(30) Foreign Application Priority Data

Jul. 23, 2021 (CN) .......................... 202110839524.X

(51) Int. Cl.
*C07H 5/06* (2006.01)
*A61K 51/04* (2006.01)
*C07B 59/00* (2006.01)

(52) U.S. Cl.
CPC ........... *C07H 5/06* (2013.01); *A61K 51/0491* (2013.01); *C07B 59/005* (2013.01); *C07B 2200/05* (2013.01)

(58) Field of Classification Search
CPC .... C07H 5/06; A61K 51/0491; C07B 59/005; C07B 2200/05

USPC ........................................................ 424/1.73
See application file for complete search history.

(56) References Cited

FOREIGN PATENT DOCUMENTS

| | | | | |
|---|---|---|---|---|
| CN | 107245087 A | 10/2017 | | |
| CN | 111138504 A | 5/2020 | | |
| CN | 112175025 A | 1/2021 | | |
| CN | 113583066 A | 11/2021 | | |
| CN | 114031652 A | 2/2022 | | |
| GB | 2570609 A | * | 7/2019 | ......... A61K 51/0491 |
| JP | 2005226021 A | * | 8/2005 | |

OTHER PUBLICATIONS

Stairs, S. et al., "Metabolic Glycan Imaging by Isonitrile-Tetrazine Click Chemistry". Chembiochem : a European journal of chemical biology, vol. 14, No. 9, May 13, 2013, ISSN:1439-4227, p. 1064, solution 1, and pp. 1063-1067.

* cited by examiner

*Primary Examiner* — Michael G. Hartley
*Assistant Examiner* — Sean R Donohue

(57) ABSTRACT

A mannose derivative is an isonitrile-containing mannose derivative of formula (I), including different linking groups X:

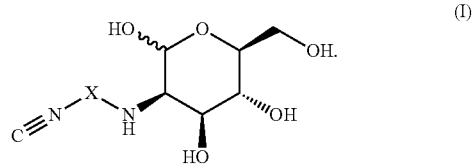

A radioactive preparation is provided, including a radiolabeled compound formed by radiolabeling the mannose derivative with a radionuclide. An application of the radioactive preparation in the diagnosis and treatment of tumors is also provided.

5 Claims, No Drawings

MANNOSE DERIVATIVE AND APPLICATION THEREOF

CROSS-REFERENCE TO RELATED APPLICATIONS

This application is a continuation of International Patent Application No. PCT/CN2022/104832, filed on Jul. 11, 2022, which claims the benefit of priority from Chinese Patent Application No. 202110839524.X, filed on Jul. 23, 2021. The content of the aforementioned application, including any intervening amendments made thereto, is incorporated herein by reference in its entirety.

TECHNICAL FIELD

This application relates to radiopharmaceutical chemistry and clinical nuclear medicine, and more particularly to a mannose derivative and an application thereof.

BACKGROUND

Currently, malignant tumors seriously endanger human health in clinic. Early diagnosis of tumors is of great practical significance for improving the survival rate and prolonging patients' life. At present, the early diagnosis of tumors is performed mainly by histological biopsy, X-ray, computerized tomography (CT), magnetic resonance imaging (MRI) and radionuclide imaging. The radionuclide imaging can reflect the physiological, pathological, metabolic and functional changes of tumors, and is non-invasive, such that it has become one of the main methods for tumor diagnosis. Especially with the integration of positron emission tomography (PET) and single-photon emission computed tomography (SPECT) with CT, the radionuclide imaging has become a predominant strategy in the nuclear medicine diagnosis.

D-Mannose is a C-2 epimer of glucose, and is a six-carbon monosaccharide. Mannose possess many biological activities, such as regulating the immune system, promoting the wound healing, avoiding some bacterial infections, inhibiting the tumor growth and metastasis, and increasing cancer survival rate. In view of this, combined with nuclear medicine imaging, mannose derivatives can be labeled with radionuclides for tumor imaging. Isocyanides are a class of organic compounds with a general formula of RNC. Carbon atoms in the isocyanides can coordinate with $^{99m}$Tc(I) to form $[^{99m}$Tc-((CNR)$_6]^+$ complexes. Among them, $^{99m}$Tc-methoxyisobutyl isonitrile ($^{99m}$Tc-MIBI), which is used as a myocardial perfusion imaging agent, can also be used as a tumor imaging agent clinically. Isocyano (—NC) can play a role as a bifunctional linker to link $^{99m}$Tc with mannose molecules, integrating a tumor-targeting sugar molecule with $^{99m}$Tc having a tracing function. Therefore, it is of great scientific significance to develop and design a $^{99m}$Tc-labeled mannose tumor molecular probe with excellent performance. Specifically, D-mannosamine hydrochloride is converted into an isonitrile-containing mannose derivative (abbreviated as CNDM), and then carbon atoms in the isonitrile ligand undergo a coordination reaction with $^{99m}$Tc to obtain a stable $^{99m}$Tc-labeled isonitrile-containing mannose derivatives for tumor imaging as a tumor imaging agent.

SUMMARY

An object of the disclosure is to provide a mannose derivative and an application thereof. The mannose derivative has excellent stability and simple preparation, and its radiolabeled product has high tumor uptake and high target-to-non-target ratio. Therefore, this application has important scientific significance and promising application prospect in the field of tumor diagnosis and treatment.

Specifically, technical solutions of the present disclosure are described as follows.

In a first aspect, a mannose derivative with a structure of formula (I) is provided:

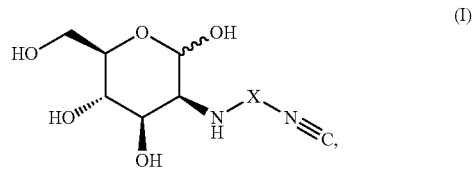

wherein X is

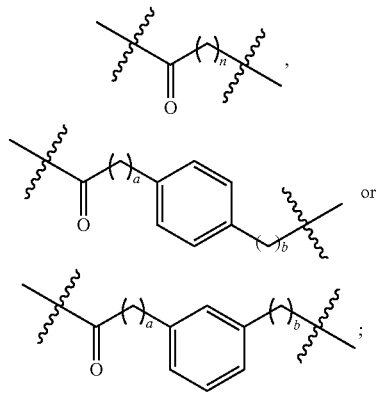

n represents an integer equal to or larger than 2; a represents an integer equal to or larger than 0; and b represents an integer equal to or larger than 0.

In some embodiments, in the above mannose derivative, when n=7, the mannose derivative has the following structural formula. A $^{99m}$Tc complex prepared from the derivative has low uptake in non-target organs, high tumor uptake and satisfactory tumor-to-blood and tumor-to-muscle ratios, exhibiting a promising prospect in the tumor diagnosis and treatment.

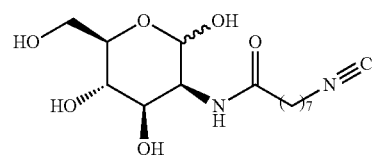

In a second aspect, a radioactive preparation is provided, comprising:
a radiolabeled compound;
wherein the radiolabeled compound is formed by labelling the mannose derivative with a radionuclide.

In some embodiments, the radionuclide is a metal radionuclide.

In some embodiments, the radionuclide is selected from the group consisting of $^{99m}$Tc, $^{99}$Tc, $^{94m}$Tc, $^{94}$Tc, $^{52}$Mn, $^{186}$Re and $^{188}$Re.

In some embodiments, the radiolabeled compound has a structure of formula (II):

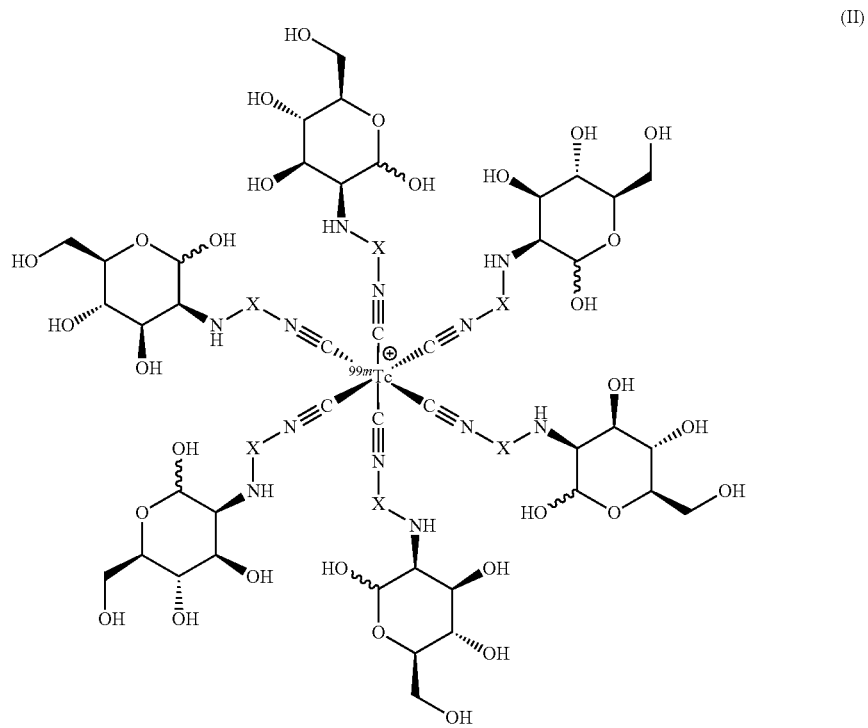

(II)

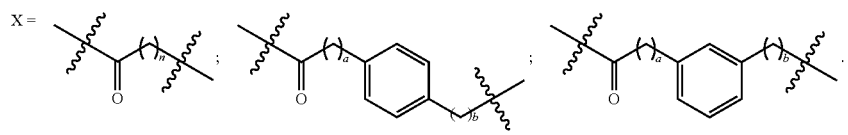

In a third aspect, this application provides a method for diagnosing and/or treating a tumor in a subject in need thereof, comprising:

administering a therapeutically-effective amount of the radioactive preparation to the subject.

The present disclosure has the following beneficial effects. The mannose derivative provided in the disclosure is labeled with the radionuclide to obtain the radioactive preparation with high tumor uptake and high target-to-non- target ratio, which is a new tumor radiopharmaceutical of promising significance.

DETAILED DESCRIPTION OF EMBODIMENTS

A mannose derivative and an application thereof are provided in the present disclosure. An embodiment of the disclosure provides a radioactive preparation with a structural general formula of $^{99m}$Tc-CNDM, as shown in the following formula:

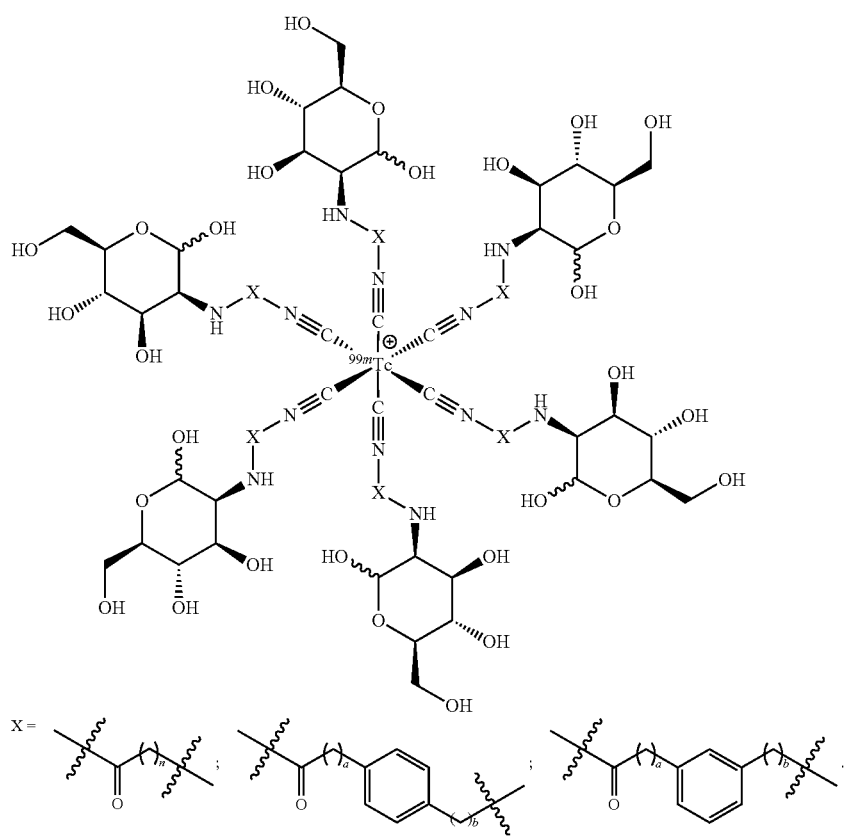

In the above formula, n represents an integer equal to or larger than 2; a represents an integer equal to or larger than 0; and b represents an integer equal to or larger than 0.

The radioactive preparation was prepared as follows.

Step (1) Synthesis of Ligand

An appropriate amount of D-mannosamine hydrochloride, NaOH and anhydrous methanol were sequentially added to a 25 mL round-bottomed flask. The reaction mixture was stirred at room temperature until the solid was completely dissolved, dropwise added into a methanol solution of a compound 1a, 1b or 1c, and reacted at room temperature for 24 h. The resultant reaction solution was distilled off under reduced pressure and purified by column chromatography (dichloromethane:methanol=5:1) to obtain the ligand CNDM.

The specific synthesis route is shown in Reaction Schemes 1-3.

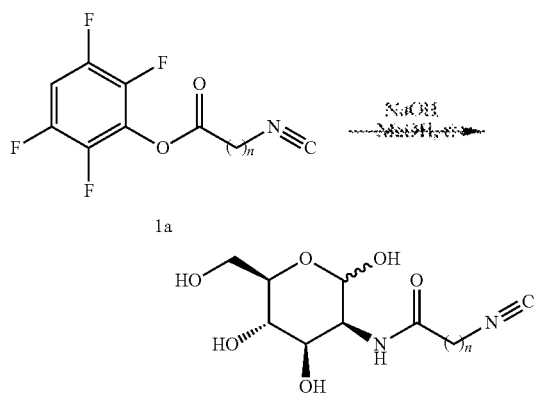

In Reaction Scheme 1, n represents an integer of 2 or more.

Reaction Scheme 1

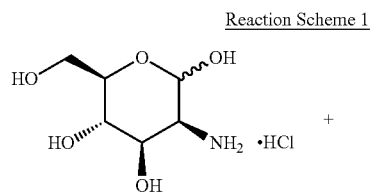

Reaction Scheme 2

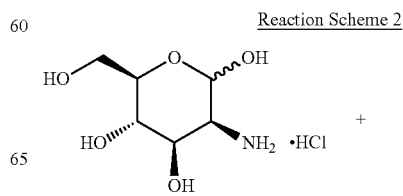

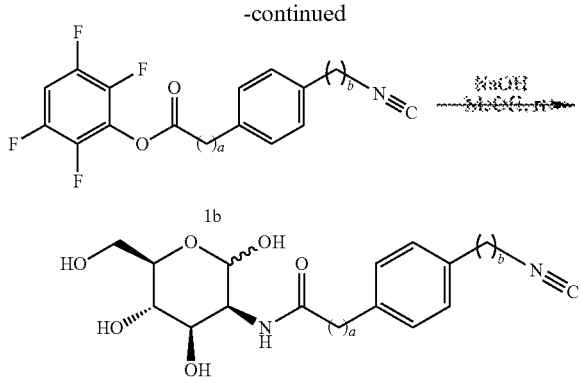

In Reaction Scheme 2, a represents an integer of 0 or above, and b represents an integer of 0 or above.

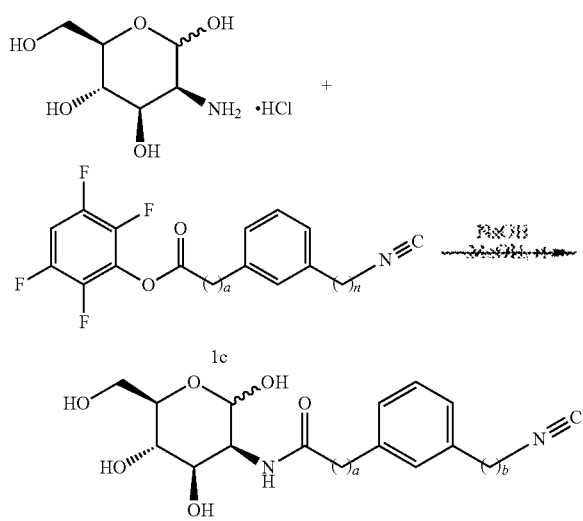

In Reaction Scheme 3, a represents an integer of 0 or above, and b represents an integer of 0 or above.

Step (2) Preparation of $^{99m}$Tc-CNDM

An appropriate amount of sodium citrate and L-cysteine were dissolved in an appropriate amount of normal saline. The mixture was sequentially added with an appropriate amount of $SnCl_2 \cdot 2H_2O$, adjusted to pH 6.0, sequentially added with an appropriate amount of the ligand CNDM and freshly-washed Na $^{99m}$TcO$_4$, and reacted at 100° C. for 20 min to obtain the $^{99m}$Tc-CNDM complex.

The $^{99m}$Tc-CNDM complex prepared by the above method has a radiochemical purity of greater than 90% and excellent in vitro and in vivo stability, and has high uptake and promising retention at the tumor site of tumor-bearing mice with a promising target-to-non-target ratio, which facilitates the promotion and application as a new tumor imaging agent.

The following embodiments are used to illustrate the invention but are not intended to limit the scope of the disclosure. If specific techniques or conditions are not specified in the embodiments, the techniques or conditions described in literature in the field shall be followed, or the product instructions shall be followed.

In the present disclosure, if the manufacturer is not indicated for the instruments used, they are all conventional products that can be purchased through regular channels. Unless otherwise stated, the methods are conventional methods, and the raw materials can be obtained from public commercial sources unless otherwise stated.

Embodiment 1

The embodiment provides a $^{99m}$Tc-labeled mannose derivative (abbreviated as $^{99m}$Tc-CN7DM), with the following formula:

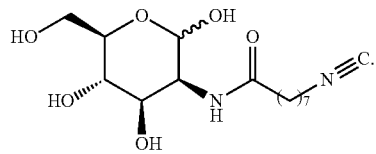

The $^{99m}$Tc-CN7DM was prepared as follows.

Step (1) Synthesis of CN7DM 0.088 g (2.2 mmol) of NaOH was added to a 25 mL round-bottomed flask and dissolved with 20 mL of methanol, and then 0.431 g (2.0 mmol) of D-mannosamine hydrochloride and 0.761 g of the compound 1a (n=7, 2.4 mmol) were added to the flask. The reaction mixture was reacted at room temperature overnight, distilled under vacuum and purified by column chromatography (dichloromethane: methanol=5:1) to obtain 0.248 g of the ligand with a yield of 38%.

$^1$H NMR (400 MHz, Methanol-d$_4$): δ 4.96 (d, J=1.6 Hz, 1H), 4.89-4.84 (m, 1H), 4.30-4.21 (m, 1H), 3.98 (dd, J=9.7, 4.7 Hz, 1H), 3.80 (dd, J=3.9, 2.5 Hz, 1H), 3.78-3.70 (m, 2H), 3.56(t, J=9.6 Hz, 1H), 3.44 (ddt, J=6.6, 3.8, 2.0 Hz, 3H), 2.25 (td, J=7.3, 2.1 Hz, 2H), 1.67-1.60 (m,4H), 1.45-1.31 (m, 8H); $^{13}$C NMR (101 MHz, Methanol-d$_4$): δ 176.78, 175.64, 153.90 (t, J=6.3 Hz), 93.68, 76.91, 73.25, 72.11, 69.27, 67.17, 66.79, 60.94, 60.75, 54.45, 53.71, 41.06 (t, J=6.0 Hz), 35.70, 35.53, 28.81, 28.72, 28.68, 28.19, 25.95, 25.49, 25.45; IR (KBr)/cm$^{-1}$ 2150.72 (—N≡C); HR-MS (ESI) for $C_{15}H_{27}N_2O_6[M+H]^+$: found 331.1861, calcd 331.1863.

Step (2) Synthesis of $^{99m}$Tc-CN7DM 2.6 mg of sodium citrate and 1 mg of L-cysteine were dissolved in an appropriate amount of normal saline. The mixture was sequentially added with 0.10 mg of $SnCl_2 \cdot 2H_2O$, adjusted to pH 6.0, sequentially added with 0.5 mg of CN7DM and 1 mL of freshly-washed Na$^{99m}$TcO$_4$, and reacted at 100° C. for 20 min to obtain the $^{99m}$Tc-CNDM described in this embodiment.

EXPERIMENTAL EXAMPLE

1. Chromatographic Identification of the Radioactive Preparation Provided in Embodiment 1

(1) Thin-Layer Chromatography (TLC)

The radiochemical yield and radiochemical purity of the radiolabeled compound were determined by TLC, where the developing system was polyamide film-ammonium acetate (1 M)/methanol in a volume ratio of 2:1. Retention factor ($R_f$) values of radioactive components were shown in Table 1.

TABLE 1

R_f value of radioactive components in polyamide film-ammonium acetate (1M)/methanol (volume ratio of 2:1) system

|  | $^{99m}TcO_4^-$ | $^{99m}TcO_2 \cdot nH_2O$ | $^{99m}Tc$-CN7DM |
|---|---|---|---|
| R_f | 0-0.1 | 0-0.1 | 0.7-1.0 |

The radiochemical yield and radiochemical purity of the $^{99m}Tc$-CN7DM complex measured by TLC were both greater than 90%, and the complex was directly used in subsequent experiments without further purification.

(2) High-Performance Liquid Chromatography (HPLC)

The radiochemical purity of the radiolabeled compound was identified by HPLC, where the HPLC parameters were listed as follows: SHIMADZU HPLC System (CL-20AVP); Kromasil C18 reversed-phase column (5 μm, 250×4.6 mm); Gabi raytest radioactivity detector; the elution gradient was shown in Table 2; flow rate: 1 mL/min; phase A: pure water containing 0.1% by volume of trifluoroacetic acid; and phase B: acetonitrile containing 0.1% by volume of trifluoroacetic acid.

TABLE 2

Gradient elution program

| t/min | A/% | B/% |
|---|---|---|
| 0 | 90 | 10 |
| 2 | 90 | 10 |
| 5 | 10 | 90 |
| 20 | 10 | 90 |
| 24 | 90 | 10 |
| 25 | 90 | 10 |

The HPLC identification results showed that a retention time of $^{99m}Tc$-CN7DM was 9.5 min.

2. Determination of Lipid-Water Partition Coefficient

To a 5 mL centrifuge tube were added 100 μL of a $^{99m}Tc$-CN7DM solution with a radioactivity of 10 μCi, 1 mL of n-octanol and 900 μL of phosphate buffered saline (PBS) (0.025 M and pH 7.4). The mixture was vortexed at a rotation speed of 2,500 rpm for 3 min, subjected to standing for stratification, and centrifuged at 9,000 rpm in a centrifuge for 5 min. Three samples (each for 100 μL) were taken from each of the two phases, and determined by a γ-counter for the radioactivity counts. The lipid-water partition coefficient P was a ratio of the organic-phase radioactivity count to the aqueous-phase radioactivity count, usually expressed as log P. The log P of $^{99m}Tc$-CN7DM was obtained as −3.15±0.06, indicating that $^{99m}Tc$-CN7DM is water-soluble.

3. Determination of Stability

The radiochemical purity of $^{99m}Tc$-CN7DM was determined by TLC after being placed in normal saline at room temperature and in mouse serum at 37° C. for 4 h. It was found that the radiochemical purity of $^{99m}Tc$-CN7DM was greater than 90% after being placed in normal saline at room temperature and in mouse serum at 37° C. for 4 h, indicating that $^{99m}Tc$-CN7DM has excellent in vitro stability.

4. Biodistribution Determination in Tumor-Bearing Mice 0.1 mL of the $^{99m}Tc$-CN7DM labeling solution (370 kBq) was injected into mice bearing S180 tumors through the tail vein. After recording the injection time, the mice were subjected to sacrificing by cervical dissection at different time points of 30 min and 120 min (5 mice were executed at each time), dissecting, taking out tissues or organs of interest such as heart, liver, lungs, kidneys, spleen, bone, muscles, small intestine, blood and tumors. A radioactivity count of each of the tissues or organs was measured by the γ-counter, and uptake value of each of the tissues or organs in % ID/g was obtained by converting a mass of each of the tissues or organs. The biodistribution results of the radiolabeled compound in tumor-bearing mice were shown in Table 3.

TABLE 3

Biodistribution results of $^{99m}Tc$-CN7DM in S180 tumor-bearing mice (n = 5, mean ± SD, % ID/g)

|  | 30 min | 120 min |
|---|---|---|
| Heart | 2.08 ± 0.26 | 1.40 ± 0.14 |
| Liver | 2.91 ± 0.23 | 2.13 ± 0.46 |
| Lung | 1.86 ± 0.19 | 0.76 ± 0.20 |
| Kidney | 6.22 ± 0.91 | 3.12 ± 0.82 |
| Spleen | 1.23 ± 0.11 | 0.80 ± 0.15 |
| Bone | 1.41 ± 0.17 | 0.76 ± 0.17 |
| Muscle | 1.88 ± 0.16 | 0.96 ± 0.12 |
| Small intestine | 1.05 ± 0.20 | 0.42 ± 0.13 |
| Tumor | 6.11 ± 0.76 | 5.92 ± 0.30 |
| Blood | 1.61 ± 0.17 | 0.09 ± 0.02 |
| Thyroid gland (% ID) | 0.04 ± 0.01 | 0.02 ± 0.00 |
| Tumor/Muscle | 3.25 | 6.18 |
| Tumor/Blood | 3.79 | 63.48 |

It can be seen from the results that $^{99m}Tc$-CN7DM has high uptake and excellent retention in tumors, while can be rapidly metabolized in non-target organs. After 120 min of administration, tumor-to-muscle and tumor-to-blood ratios are high. In particular, $^{99m}Tc$-CN7DM can be rapidly cleared from the blood, thereby greatly increasing the tumor-to-blood ratio.

Although the present disclosure has been described in detail above with reference to embodiments, those skilled in the art can still make some modifications or improvements to the technical solutions disclosed herein. It should be understood that those modifications or improvements made without departing from the spirit of the disclosure (for example, radioactive preparations obtained by radiolabeling a ligand formed by structurally modifying monosaccharides other than glucose and mannose) shall fall within the scope of the disclosure defined by the appended claims.

What is claimed is:

1. A mannose derivative with a structure of formula (I):

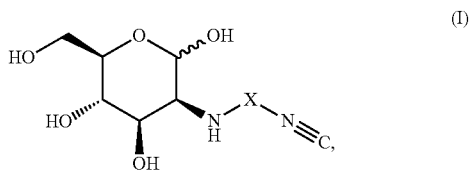

wherein X is

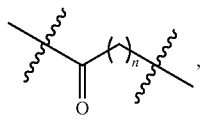

and n is 7.

2. A radioactive preparation, comprising:
a radiolabeled compound;
wherein the radiolabeled compound is formed by labelling the mannose derivative of claim 1 with a radionuclide.

3. The radioactive preparation of claim 2, wherein the radionuclide is selected from the group consisting of $^{99m}$Tc, $^{99}$Tc, $^{94m}$Tc, $^{94}$Tc, $^{52}$Mn, $^{186}$Re and $^{188}$Re.

4. The radioactive preparation of claim 3, wherein the radiolabeled compound has a structure of formula (II):

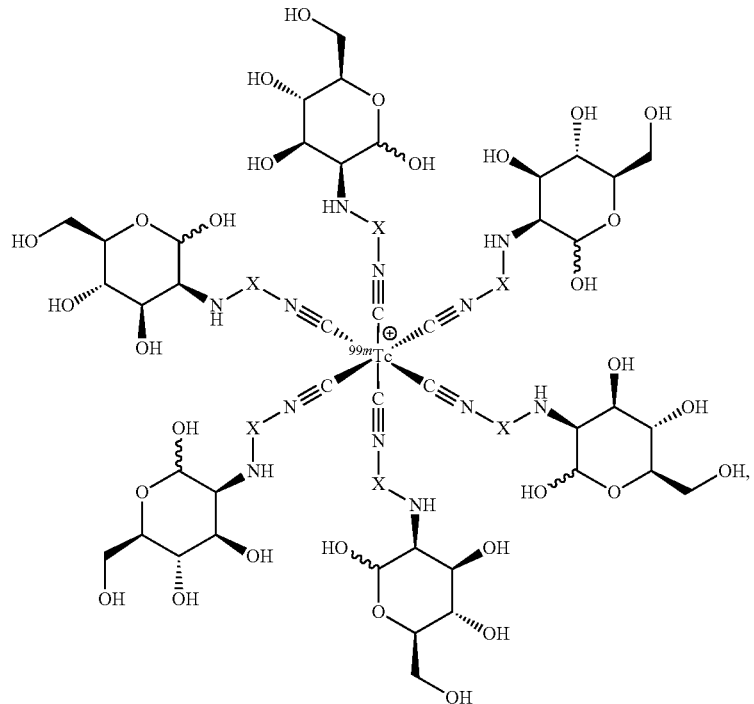

(II)

wherein X is

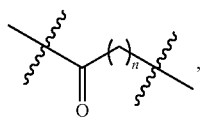

and n is 7.

5. A method for diagnosing and/or treating a tumor in a subject in need thereof, comprising:
administering a therapeutically-effective amount of the radioactive preparation of claim 2 to the subject.

* * * * *